US012564660B2

(12) United States Patent
Moalli et al.

(10) Patent No.: US 12,564,660 B2
(45) Date of Patent: Mar. 3, 2026

(54) BIOFABRICATION OF VAGINAL SUPPORT USING VAGINALLY DERIVED CELLS

(71) Applicant: Magee-Womens Research Institute and Foundation, Pittsburgh, PA (US)

(72) Inventors: Pamela Moalli, Pittsburgh, PA (US); Vivian Sung, Providence, RI (US); Jeffrey Morgan, Sharon, MA (US)

(73) Assignee: Magee-Womens Research Institute & Foundation, Pittsburgh, PA (US)

( * ) Notice: Subject to any disclaimer, the term of this patent is extended or adjusted under 35 U.S.C. 154(b) by 268 days.

(21) Appl. No.: 18/426,754

(22) Filed: Jan. 30, 2024

(65) Prior Publication Data

US 2024/0252720 A1      Aug. 1, 2024

Related U.S. Application Data

(60) Provisional application No. 63/482,371, filed on Jan. 31, 2023.

(51) Int. Cl.
*A61L 27/36*      (2006.01)
*A61L 27/26*      (2006.01)

(52) U.S. Cl.
CPC ........... *A61L 27/3679* (2013.01); *A61L 27/26* (2013.01); *A61L 27/3604* (2013.01); *A61L 27/3633* (2013.01)

(58) Field of Classification Search
CPC .................................................. A61L 2430/22
See application file for complete search history.

(56) References Cited

PUBLICATIONS

Pavlov et al., Experimental morphological rationale for the use of cultures of multipotent mesenchymal stem cells in combination with biomaterials in the reconstruction of the pelvic floor. Urologiia (Moscow, Russia : 1999), (Sep. 2019) No. 4, pp. 32-37 (Year: 2019).*

* cited by examiner

*Primary Examiner* — Qiuwen Mi
(74) *Attorney, Agent, or Firm* — Buchanan Ingersoll & Rooney PC

(57) ABSTRACT

Embodiments relate to a living tissue graft derived from autologous cells used to provide support or to strengthen/ reinforce compromised tissue. The living tissue graft comprises both cells and extracellular matrix (ECM) and overcomes problems related to foreign body responses to synthetic materials and rejection reactions to allograft tissue.

10 Claims, 9 Drawing Sheets

* Nonadhesive hydrogel is cast from a micromold

* Cells seeded into trough of the micromold; inability to adhere to hydrogel drives self assembly into a multi-cellular structure (basic subunit)

* Cells within the subunit generate tension causing them to align, elongate and synthesize ECM

* Organization of the ECM is dictated by the mechanical cues set by the micromold

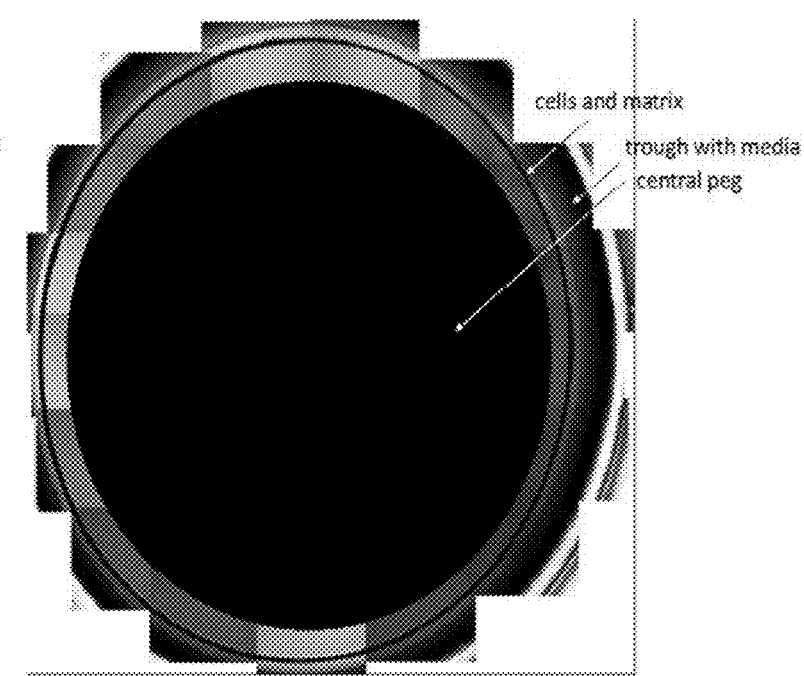

FIG. 1

Basic subunit is biofabricated on an agarose mold from ~ 2 million cells. As shown in (A) Rapid contraction and twisting occurs within the first minute of removal from agarose mold. After testing many conditions, we found that residual stress in microtissues reduced with cold temperatures (B).

Workflow to tissue biofabrication. Cells are seeded onto a nonadhesive micromold. Not able to adhere, the cells self organize into a basic subunit comprised of cells and matrix. Fusion of multiple subunits in the x, y, and z planes results in formation of a living tissue for use in prolapse surgeries.

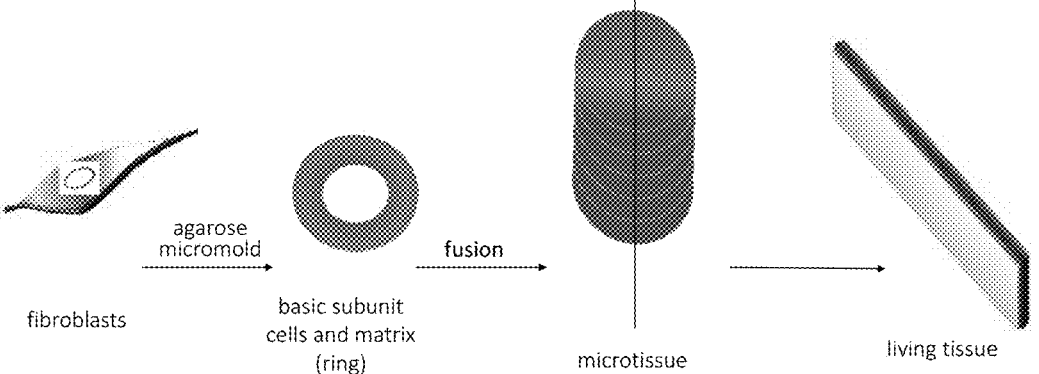

fibroblasts → agarose micromold → basic subunit cells and matrix (ring) → fusion → microtissue → living tissue

FIG. 5

3 day          6 day          9 day microtissues fabricated from fused living subunits at 3, 6,
and 9 days post fabrication.

Twisting of 10 cm subunits to
increase mechanical integrity

BIOFABRICATION OF VAGINAL SUPPORT USING VAGINALLY DERIVED CELLS

CROSS-REFERENCE TO RELATED APPLICATIONS

This patent application claims the benefit of and priority to U.S. Provisional Patent Application No. 63/482,371, filed on Jan. 31, 2023, the entire contents of which are incorporated by reference in its entirety.

STATEMENT REGARDING FEDERALLY SPONSORED RESEARCH

This invention was made with U.S. Government support under Grant No. HD069006 by the National Institute of Health. The Government has certain rights in the invention.

FIELD OF THE INVENTION

Embodiments relate to a living tissue graft, and particularly to a living tissue graft derived from autologous cells used to provide support or to reinforce/strengthen compromised tissue.

BACKGROUND OF THE INVENTION

Pelvic organ prolapse (POP) is a common life altering condition for women in which failure of support to the vagina causes the organs supported by it to prolapse or fall into the vaginal lumen. An estimated 300,000 prolapse surgeries are performed annually in the United States. Unfortunately, POP repairs using a patient's own tissues have high failure rates (up to 40-60% at 5 years), prompting surgeons to seek materials to augment repairs, most commonly polypropylene mesh. While current practice-based research supports the use of lightweight, knitted, wide pore polypropylene when mesh is used for prolapse repairs, the ideal mesh has not been defined and no mesh to date is without complications. Complications related to polypropylene mesh are similar to other soft tissue-biomaterial interactions that occur as a result of the long-term inflammatory response related to the presence of a foreign material. In addition, polypropylene is orders of magnitude stiffer than the vagina resulting in thinning and atrophy of grafted tissues. In women with POP, the vagina and the tissues that support it are already structurally and functionally compromised.

Therefore, a solution that restores rather than further deteriorates the vagina is highly desirable.

Moreover, support to the top of the vagina, or apical support, is classically provided by the cardinal-uterosacral ligament (USL) complex. The anatomical landmarks of this complex have been studied in cadavers and in women during surgery, and more recently, using computed tomography and magnetic resonance imaging. Histologically, the USL is a multifaceted, mesenteric-like structure containing abundant smooth muscle and smaller amounts of loose connective tissue, vessels, and nerve bundles with a progressive decrease in the quantity of smooth muscle along the superficial, middle, and deep portions of the ligament. From the vaginal apex/cervix to its origin at the sacrum, the ligament has been estimated to range from 8 to 14 cm in length. While the mechanism by which the USL complex becomes injured and fails in its supportive capacity is not clear, as stated above, surgeries which restore support to the apex are associated with improved outcomes.

Thus, in theory, replacement or augmentation of the vaginal supportive tissues with self-derived biofabricated tissue with similar properties, but with improved supportive capacity, provides a novel solution to prolapse repair.

Accordingly, the present application is directed towards biofabrication of a living tissue graft ex vivo for use in prolapse surgeries to re-establish support to the vagina. This approach employs vaginally derived cells to biofabricate living tissue grafts with functional properties similar to native vagina.

This solution can be applied to other complications. For example, regarding stress urinary incontinence (SUI), mid-urethral sling (MUS) is the first-line surgical treatment for SUI with urethral hypermobility after the failure of pelvic floor muscle training. Around 13.6% of women will undergo surgery for SUI during their lifetime. Retropubic mid-urethral slings (RP-MUS) and transobturator mid-urethral slings (TO-MUS) are widely used procedures for the surgical treatment of female SUI, yielding high cure rates. However, there are concerns about the safety of these devices linked to persistent and/or chronic pain. Concerns about the safety and effectiveness of have led regulatory bodies to limit their use in Europe, Australia, and New Zealand leaving fewer options for patients and their surgeons.

Further, regarding hernia repair, abdominal wall hernias are common with a prevalence of 4% in the general population, and groin hernias are particularly common accounting for ~70% of abdominal hernias with a lifetime risk of 27% in men and 3% in women. Mesh repair reduces the risk of hernia recurrence relative to non-mesh repair and, consequently, is often used. Meshes used in hernia repair are primarily comprised of large pored light weight polypropylene. Complications related to mesh are pain, encapsulation, migration, and erosion into an adjacent organ. Chronic postherniorrhaphy groin pain (defined as pain lasting >3 months) has emerged as the most important postoperative issue reported by patients undergoing groin hernia mesh augmented repair. Although the incidence varies widely in the literature (1.5 to 54%), the consensus is that approximately 10% of patients who have undergone an inguinal herniorrhaphy have some chronic pain. Currently, about one million meshes are used per year for hernia repairs globally.

Further, mastopexy involves manipulation of the breast parenchyma to improve the longevity of breast ptosis correction. Mesh support of the ptotic breast is an extension of this surgical practice and aims to restore the lost strength of the support structures of the breast.

Overall, while synthetic meshes have been widely adopted to improve surgical outcomes over native tissue repairs, meshes have also been associated with a higher-than-expected complications.

As mentioned above, rebuilding or replacing the weakened tissues from a patient's own cells in the form of a living tissue graft is appealing to both patients and surgeons.

Cell based methods are emerging as a viable approach to recapitulate the native structure and function of regenerated tissues. When properly organized into a suitable three-dimensional architecture, cell-based constructs are able to synthesize, secrete and mature a biochemically and mechanically complex extracellular matrix (ECM) that more closely mimics native tissue compared to synthetic scaffolds such as polypropylene. Moreover, this native, biocompatible structure made with the patient's own cells is better able to promote proper tissue integration due to the absence of a foreign body response. Xenograft biologic scaffolds such as Biodesign® (porcine intestine, Cook Medical) and Gentrix® (porcine urinary bladder matrix, Integra Life Sciences) are derived from pig and therefore evoke a strong foreign body response particularly against the alpha-gal epitope. Alloderm™ (LifeCell Corp) is derived from cadaveric skin and has the potential to transmit harmful diseases and will vary in quality based on the health of the donor.

The use biopsies of tissue (e.g., the vagina) to construct a living graft for prolapse (and other complications/surgeries) that will provide both vaginal reinforcement and apical support is advantageous because it is easily accessible, easy to standardize, and does not leave a noticeable scar at the biopsy site. The biopsy could alternatively be obtained from skin to avoid the need to obtain tissue from the fascial supports.

Ultimately, this disclosure relates to a device used in reconstructive surgeries where a graft is needed to provide support or to reinforce/strengthen compromised tissue. The graft is derived from autologous cells and is living, and therefore overcomes problems related to the foreign body response to synthetic materials and rejection reactions to allograft.

The present disclosure is directed toward overcoming one or more of the above-mentioned problems, though not necessarily limited to embodiments that do.

SUMMARY OF THE INVENTION

Embodiments relate to a living tissue graft derived from autologous cells used to provide support or to strengthen/reinforce compromised tissue. The living tissue graft comprises both cells and extracellular matrix (ECM) and overcomes problems related to foreign body responses to synthetic materials and rejection reactions to allograft tissue.

In an exemplary embodiment, a method for treating damaged tissue comprises replacing or augmenting the damaged tissue by the steps of: preparing a living tissue graft derived from said tissue; and implanting, transplanting, administering, applying, adhering or affixing the living tissue graft onto the damaged tissue, wherein the step of preparing the living tissue graft comprises: preparing a plurality of subunits comprising cells isolated from the damaged tissue and extracellular matrix; fusing the plurality of subunits to form a plurality of microtissue units; and assembling the plurality of microtissue units to form the living tissue graft.

In some embodiments, the damaged tissue is vaginal tissue.

In some embodiments, the plurality of subunits are prepared by seeding a micro-mold with the cells isolated from the damaged tissue.

In some embodiments, the micro-mold comprises agarose.

In some embodiments, the plurality of subunits are ring-shaped.

In some embodiments, the plurality of subunits have a diameter greater than or equal to 30 mm.

In some embodiments, the step of fusing the plurality of subunits to form microtissue units comprises stacking the plurality of subunits around a peg.

In some embodiments, the peg comprises polytetrafluoroethylene and agarose.

In some embodiments, the method further comprises cooling the plurality of subunits prior to fusing.

In some embodiments, the diameter of the plurality of subunits is greater than the diameter of the peg.

Additional features, aspects, objects, advantages, and possible applications of the present disclosure will become apparent from a study of the exemplary embodiments and examples described below, in combination with the Figures and the appended claims.

BRIEF DESCRIPTION OF THE DRAWINGS

The above and other objects, aspects, features, advantages and possible applications of the present innovation will be more apparent from the following more particular description thereof, presented in conjunction with the following drawings. Like reference numbers used in the drawings may identify like components.

FIG. 1 shows the synthesis of a subunit.

FIG. 5 shows the biofabrication of a living tissue graft,

DETAILED DESCRIPTION OF THE INVENTION

Figure 2:
FIG. 2 shows exemplary materials used to make micro-mold system and the micro-mold system itself.

The following description is of exemplary embodiments that are presently contemplated for carrying out the present invention. This description is not to be taken in a limiting sense, but is made merely for the purpose of describing the general principles and features of various aspects of the present invention. The scope of the present invention is not limited by this description.

Embodiments relate to a living tissue graft. The living tissue graft may be used to reinforce/augment weakened supportive tissues. In particular, the living tissue graft may be used in surgical procedures relating to conditions including, but not limited to, pelvic organ prolapse, stress urinary incontinence, hernias, breast reconstruction (mastopexy) and other like conditions.

Embodiments further relate to a method for preparing the living tissue graft, the method comprising: (i) preparing a plurality of subunits; (ii) fusing the plurality of subunits to form a plurality of microtissue units; and (iii) assembling the plurality of microtissue units to form the living tissue graft.

The living tissue graft comprises a plurality of subunits. A subunit is a custom-designed three-dimensional multicellular structure derived from autologous cells. A subunit may have dimensions between 30-120 mm×0.1-0.4 mm and comprise 1-10 million cells.

In particular, the subunit is derived from tissue/skin fibroblasts isolated from a 7-12 mm biopsy. For example, the biopsy may be obtained using a biopsy punch (Acuderm, 12 mm). Once the biopsy is obtained, it may be placed into cell culture media under sterile conditions and placed on ice. Exemplary cell culture media includes, but is not limited to, 14% FBS in DMEM/F-12 (high glucose), 1% pen/strep, 1.5% amphotericin on ice.

It is contemplated that a subunit is synthesized using an ex-vivo micro-mold system. A person of ordinary skill in the art would appreciate that the ex-vivo micro-mold system is a scaffold free approach. A micro-mold system directs cells to self-assemble into a custom-designed three-dimensional subunit. The micro-mold system is produced from a non-adhesive hydrogel (e.g., agarose, polyacrylamide, or any other suitable non-adhesive hydrogel) such that cells are prevented from adhering to the micro-mold system. By virtue of this design, the micro-mold system may then control the alignment of cells.

As seen in FIG. 1, the micro-mold system comprises a trough surrounding a central peg. Organization of the subunit is dictated by the mechanical cues set by the micro-mold system, particularly by the trough/central peg. Cells derived from a vaginal/skin biopsy (i.e., fibroblasts) and in standard cell culture media (e.g., 14% FBS in DMEM/F-12) at 37° C. are seeded into the trough, and the cells inability to adhere to the central peg (e.g., due to its non-adhesive nature) drives self-assembly and alignment of the cells around the central peg, thereby forming the subunit. It is contemplated that the cells around the central peg and forming the subunit generate tension, thus causing the cells to align, elongate, and secrete their own extracellular matrix (ECM). Accordingly, the subunit comprises both cells and ECM.

In an exemplary method of making the micro-mold system, as seen in FIG. 2, a circular stainless-steel mold, a stainless-steel cylinder, and a non-adhesive hydrogel (e.g., agarose) are used to make the subunits. In particular, the cylinder may be placed on a dish, and molten agarose may be poured into the dish. The mold is then inverted and placed on top of the dish. When the agarose solidifies, the cylinder and the circular mold are both removed. The resulting agarose mold comprises a central well configured to accommodate cell culture media and a circular trough. After the agarose is equilibrated by several changes of cell culture media, the culture media in the trough is removed and cells are seeded into the circular trough. The cells settle to the bottom of the trough. Unable to attach to the agarose, the cells aggregate and self-assemble to form a ring-shaped subunit with measurements that are dictated by the geometry of the circular trough/central peg. The circular trough as seen in FIG. 2 has an inner diameter of 64 mm and a circumference of 200 mm.

It is contemplated that the cross-sectional shape (e.g., ring-shaped) of the central peg dictates the shape of the formed subunit. It is contemplated that the central peg will direct the formation of a ring-shaped subunit.

It is contemplated that the outer diameter of the central peg (and inner diameter of the trough) is between 30-120 mm. Accordingly, the subunits may also have diameters between 30-120 mm. This correlates to a circumference between 94-377 mm.

While the present micro-mold system is described with a central peg, it is contemplated that the mold may comprise a central structure of any shape (e.g., honeycomb shaped, fan shaped, or any other suitable shape). It is contemplated that the shape of the central structure dictates the shape of the formed subunit. The central structure may be of any shape with varying sizer.

After the subunit is formed, the subunit is matured for 7-14 days. The maturation process is a natural process wherein the cells in the subunit require time to synthesize, secrete, and assemble ECM, such as the collagen family of proteins. The ECM provides mechanical strength to the subunit and living tissue graft. As mentioned above, the maturation process simply requires waiting on the order of 7-14 days so that the subunits have enough mechanical strength to allow for their handling and manipulation.

Figure 3:
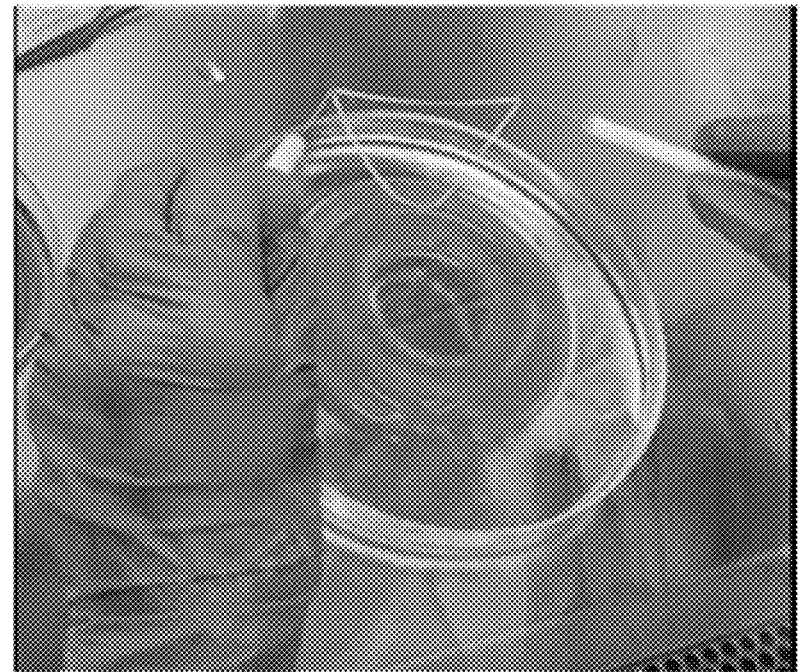
FIG. 3 shows the removal of a subunit from the micro-mold system.

After the subunit is formed and matured, the subunit is removed from the mold for further processing. As seen in FIG. 3, the subunit may be pried from the mold using two small metal hooks or any other suitable tool. It is contemplated that a portion of the mold may be cut in order to provide better access to the subunit for removal.

It is contemplated that the above-described micro-mold technology can make living building parts in a wide range of diverse sizes and shapes in a layer-by-layer strategy to build living tissue grafts of almost unlimited size and shape.

Figure 4:
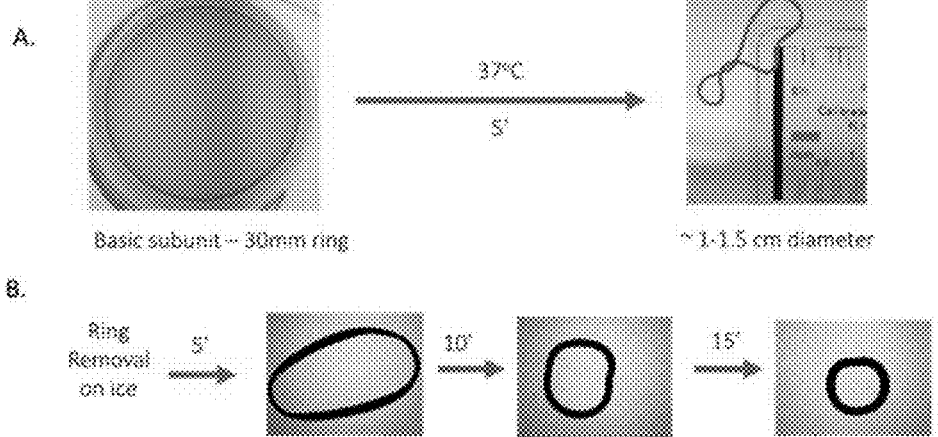
FIG. 4 shows the synthesis of a subunit.
Figure 6:
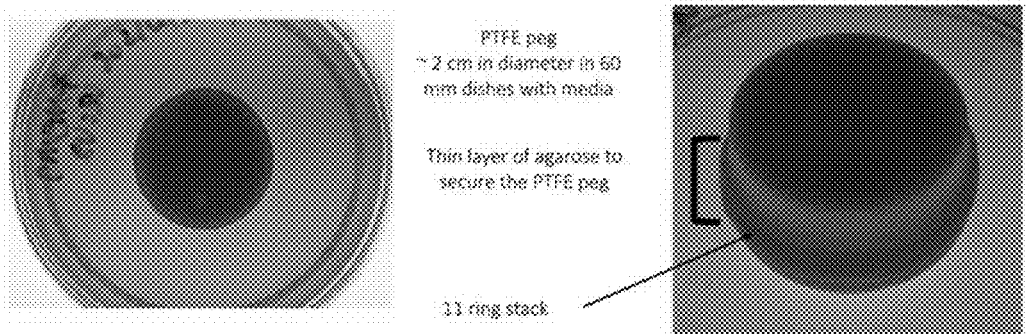
FIG. 6 shows fusion of subunits in the z-plane to create a microtissue unit.
Figure 7:
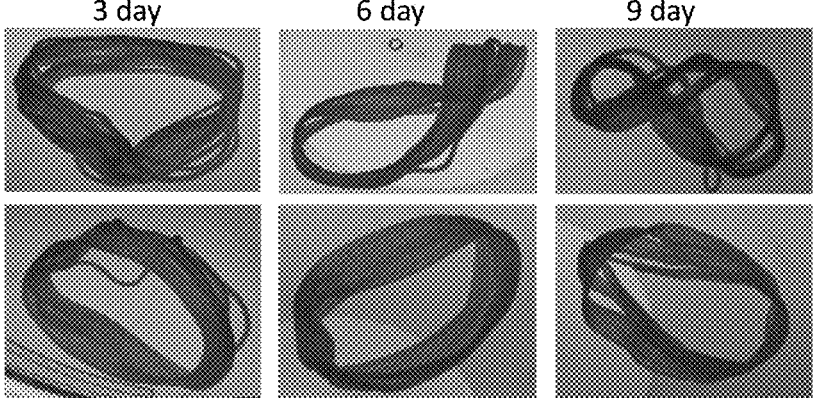
FIG. 7 shows microtissue units fabricated from fused subunits at 3, 6, and 9 days post-fabrication.

As seen in FIG. 4, after the subunit is removed from the mold, rapid contraction and twisting of the subunit may occur. It is further contemplated that exposing the subunit to cold temperatures (e.g., between 0-4° C.) may reduce the residual stress in the subunit such that rapid contraction and twisting may be avoided and/or inhibited. For example, after the subunit is removed from the mold, the subunit may be placed on ice to avoid and/or inhibit rapid contraction and twisting.

It is contemplated that the structural stiffness of the subunit should be enough such that the subunit and resulting living tissue graft may be readily handled and secured into place by a surgeon and should approximate the structural properties of the ligament/tissue it seeks to replace. However, the structural stiffness of the subunit and resulting living tissue graft does not have to equal that of the ligament/tissue it is replacing because it is expected that after the graft is implanted, the host's tissue will increase the mechanical properties of the graft. For example, the subunit may have a structural stiffness between 30-100 KPa.

As seen in FIG. 5, a microtissue unit may be formed by fusing a plurality of subunits, preferably by fusing a plurality of subunits in the x, y, and z planes. Fusion is a natural process that occurs between cells when they are unable to adhere to an underlying substrate. A microtissue unit may have dimensions between 30-120 mm×1-4 mm and comprise 20-30 subunits and/or 40-100 million cells.

In an exemplary embodiment, a microtissue unit may be synthesized using a non-adhering peg. In particular, the non-adhering peg may be positioned in non-adhering hydrogel emersed in standard cell culture media (e.g., 14% FBS in DMEM/F-12) at 37° C. Moreover, a subunit may be placed around the non-adhering peg. Accordingly, it is contemplated that the non-adhering peg may have a diameter smaller than the diameter of the subunit. For example, if the diameter of the subunit is 30 mm, the non-adhering peg may have a diameter less than 30 mm, such as 20 mm.

The non-adhering peg may direct subunits to contract around the peg. In particular, a subunit has residual stress causing it to contract, and the non-adhering peg allows subunits to contract around the peg. After a first subunit contracts around the peg, a second subunit may be added such that the second unit similarly contracts around the peg and fuses with the first subunit in the z direction. This may be repeated until a stack of subunits are fused around the peg to create the microtissue unit. It is contemplated that 10-30 subunits may be stacked to form a microtissue unit.

Figure 8:
FIG. 8 shows twisting of 10 cm subunits to increase mechanical integrity.

In an exemplary embodiment, a plurality of subunits may undergo a twisting process. As seen in FIG. 8, a twisting device may be used to twist the subunits. The twisting device may be a biochamber filled with standard cell culture media (e.g., 14% FBS in DMEM/F-12), in which the plurality of subunits are suspended to two hooks positioned at either end of the chamber. Rotation of the hooks produces the desired twisting without disruption of the subunits. Advantageously, the twisting process achieves at least three goals. First, it carefully assembles/fuses multiple subunits into a single, easy-to-use microtissue unit whose ultimate tensile strength increases with each subunit added. Second, it blends the mechanical properties of individual subunits into a single unit such that no single subunit is the weakest link (a similar process is conducted when strands of rope are twisted). Third, the subunits are brought into close contact such that their living surfaces may fuse with each other and the cells on the surface can synthesize, secrete, and assemble ECM proteins that bind the subunits together, thus further increasing the mechanical properties of the microtissue.

As explained above, while it is contemplated that the micro-mold system may comprise a central structure of any shape, it is contemplated that a central peg and a corresponding ring-shaped subunit is conductive to the above-described twisting process.

Figure 9:
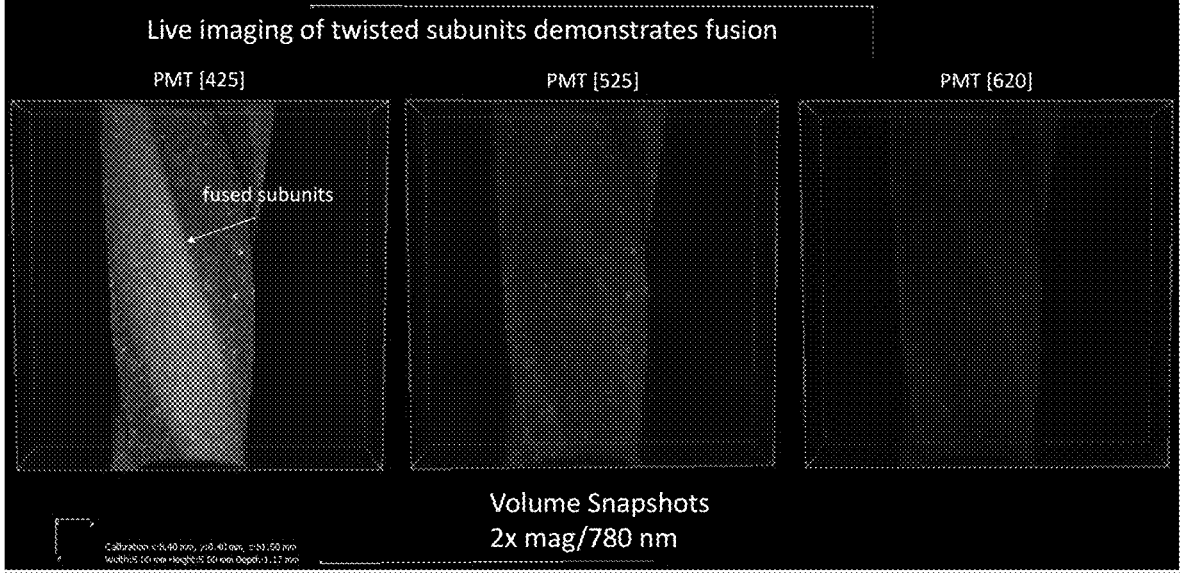
FIG. 9 shows multiphoton imaging of twisted subunits as evidence of fusion.

As seen in FIG. 9, multiphoton imaging of the subunits demonstrated twisted subunits as evidenced by variation in color with evidence of fusion. Second harmonic generation showed dense highly aligned collagen predominant matrix. Fibroblasts were present within the matrix and aligned in the direction of the collagen fibers.

A living tissue graft may be formed from a plurality of microtissues. A living tissue graft may have dimensions between 30-120 mm×40-100 mm×3-10 mm and comprise 200-400 subunits and/or 300-800 million cells.

To synthesize the living tissue graft, a plurality of microtissues may be placed side-by-side as well as on top of each other while submerged in cell culture media (e.g., 14% FBS in DMEM/F-12) at 37° C. Fusion of the plurality of microtissues into the living tissue graft takes place within 24 hours. Fusion is a natural process that occurs between cells. As the living tissue graft essentially comprises a plurality of subunits, it is contemplated that the living tissue graft comprises both cells and ECM.

Multiple strategies may be employed to form a full-sized living tissue graft. For example, thickness may be expanded by stacking additional layers of subunits in the x and y dimensions with consecutively larger subunits (e.g., 35 mm, 40 mm, and 45 mm). Moreover, ring-shaped subunits may be opened at 4° C. (the temperature at which the subunits remain flat), and fusion of the flat subunits in the x and y planes may also be performed. The purpose of opening the ring-shaped subunits is to achieve a broad flat living tissue graft (see FIG. 5). The use of reversible small molecular inhibitors may also be used to keep tissues flat during fusion.

This technology can easily be scaled up for biomanufacturing purposes. The living tissue graft may be used to reinforce/augment damages supportive tissues in a prolapse or hernia repair or breast lift. Treating damaged tissue comprises preparing a living tissue graft derived from said tissue, and implanting, transplanting, administering, applying, adhering or affixing the living tissue graft onto the damaged tissue. The cells and newly synthesized ECM are expected to integrate into the target tissue in a constructive remodeling response and in the absence of a foreign body response.

It is contemplated that the living tissue graft may be secured in place by a surgeon using standard, well-known means.

It is contemplated that the living tissue graft may be used alone or in conjunction with a synthetic mesh (e.g., any standard, well-known mesh) to promote tissue integration.

EXAMPLES

The following examples serve to illustrate certain aspects of the disclosure and are not intended to limit the disclosure.

Example 1

To test the feasibility of biofabricating living grafts from a small vaginal biopsy sent from an outside location, a study was developed in which biopsies were procured from various locations across the United States. 8-10 mm biopsies were successfully collected from Brown University, Duke University, University of California San Diego, University of Alabama, and University of Pennsylvania. Biopsies were sent in media in specialized containers with 48 hrs of cooling. N=30 were collected and all were viable at delivery. 30 basic subunits were successfully biofabricated from approximately 2 million cells obtained in primary fibroblast cultures. Cells were expanded to 50-70 million in 15 of the primary cultures for fabrication of 15 microtissues. A sufficient number of cells (400-500 million) were generated for biofabrication of a microtissue from 5 of the biopsies (randomly selected). Evidence of senesce was not observed in any of the cultures. These cells are grown in standard tissue culture conditions at 37° C. and experiments were performed in standard culture media (14% FBS in DMEM/F-12).

It should be understood that modifications to the embodiments disclosed herein can be made to meet a particular set of design criteria. For instance, the number of or configuration of components or parameters may be used to meet a particular objective.

It will be apparent to those skilled in the art that numerous modifications and variations of the described examples and embodiments are possible in light of the above teachings of the disclosure. The disclosed examples and embodiments are presented for purposes of illustration only. Other alternative embodiments may include some or all of the features of the various embodiments disclosed herein. For instance, it is contemplated that a particular feature described, either individually or as part of an embodiment, can be combined with other individually described features, or parts of other embodiments. The elements and acts of the various embodiments described herein can therefore be combined to provide further embodiments.

It is the intent to cover all such modifications and alternative embodiments as may come within the true scope of this invention, which is to be given the full breadth thereof. Additionally, the disclosure of a range of values is a disclosure of every numerical value within that range, including the end points. Thus, while certain exemplary embodiments of the device and methods of making and using the same have been discussed and illustrated herein, it is to be distinctly understood that the invention is not limited thereto but may be otherwise variously embodied and practiced within the scope of the following claims, which is to be given the full breath thereof.

What is claimed is:

1. A method for treating damaged tissue, said method comprising replacing or augmenting the damaged tissue by the steps of:

preparing a living tissue graft derived from said damaged tissue; and implanting, transplanting, administering, applying, adhering or affixing the living tissue graft onto the damaged tissue, wherein the step of preparing the living tissue graft comprises:

preparing a plurality of subunits comprising cells isolated from the damaged tissue and extracellular matrix;

fusing the plurality of subunits to form a plurality of microtissue units; and assembling the plurality of microtissue units to form the living tissue graft.

2. The method of claim 1, wherein the damaged tissue is vaginal tissue.

3. The method of claim 1, wherein the plurality of subunits are prepared by seeding a micro-mold with the cells isolated from the damaged tissue.

4. The method of claim 1, wherein the micro-mold comprises agarose.

5. The method of claim 3, wherein the plurality of subunits are ring-shaped.

6. The method of claim 5, wherein the plurality of subunits have a diameter greater than or equal to 30 mm.

7. The method of claim 1, wherein the step of fusing the plurality of subunits to form microtissue units comprises stacking the plurality of subunits around a peg.

8. The method of claim 7, wherein the peg comprises polytetrafluoroethylene and agarose.

9. The method of claim 1, further comprising cooling the plurality of subunits prior to fusing.

10. The method of claim 7, wherein the diameter of the plurality of subunits is greater than the diameter of the peg.

\* \* \* \* \*